(12) United States Patent
Dambrine et al.

(10) Patent No.: US 9,365,531 B2
(45) Date of Patent: Jun. 14, 2016

(54) METHOD FOR SELECTIVELY OXIDIZING 5-HYDROXYMETHYL FURALDEHYDE

(71) Applicants: Laurent Dambrine, Sains en Gohelle (FR); Mathias Ibert, La Chapelle d'armentieres (FR)

(72) Inventors: Laurent Dambrine, Sains en Gohelle (FR); Mathias Ibert, La Chapelle d'armentieres (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/368,143

(22) PCT Filed: Dec. 18, 2012

(86) PCT No.: PCT/FR2012/052967
§ 371 (c)(1),
(2) Date: Jun. 23, 2014

(87) PCT Pub. No.: WO2013/093322
PCT Pub. Date: Jun. 27, 2013

(65) Prior Publication Data
US 2014/0378691 A1   Dec. 25, 2014

(30) Foreign Application Priority Data
Dec. 22, 2011 (FR) ...................................... 11 62343

(51) Int. Cl.
*C07D 307/48* (2006.01)
*C07D 307/46* (2006.01)

(52) U.S. Cl.
CPC ............ *C07D 307/48* (2013.01); *C07D 307/46* (2013.01)

(58) Field of Classification Search
USPC ......................................................... 549/502
See application file for complete search history.

(56) References Cited

U.S. PATENT DOCUMENTS

| 4,339,387 A | 7/1982 | Fleche et al. |
| 4,590,283 A | 5/1986 | Gaset et al. |
| 2011/0251399 A1 | 10/2011 | Dingerdissen et al. |

FOREIGN PATENT DOCUMENTS

| FR | 2464260 A1 | 3/1981 |
| FR | 2551754 A1 | 3/1985 |
| WO | 0134657 A1 | 5/2001 |
| WO | 03024947 A1 | 3/2003 |
| WO | 2008054804 A2 | 5/2008 |
| WO | 2010089213 A1 | 8/2010 |
| WO | 2010132740 A2 | 11/2010 |
| WO | 2011124639 A1 | 10/2011 |
| WO | 2012004069 A1 | 1/2012 |

OTHER PUBLICATIONS

Machine translation of WO 2012004069 A1 (Jan. 12, 2012).*
Cottier et al., "Oxidation of 5-Hydroxymethylfurfural and Derivatives to Furanaldehydes with 2,2,6,6-Tetramethylpiperidine Oxide Radical—Co-oxidant Pairs", Journal of Heterocyclic Chemistry, 1995, vol. 32, No. 3, XP002378550.
International Search Report, dated Feb. 21, 2013, from corresponding PCT application.

* cited by examiner

*Primary Examiner* — Kristin Vajda
(74) *Attorney, Agent, or Firm* — Young & Thompson

(57) ABSTRACT

A method for oxidizing 5-hydroxymethyl furaldehyde, includes at least one step of oxidation in the presence of an organic acid, a nitroxyl radical, an oxygen source, and an oxygen transfer agent.

16 Claims, No Drawings

METHOD FOR SELECTIVELY OXIDIZING 5-HYDROXYMETHYL FURALDEHYDE

FIELD OF THE INVENTION

The present invention relates to a novel process for the oxidation of 5-hydroxymethyl furaldehyde (5-HMF). The oxidation product of 5-HMF selectively formed after this process is furan-2,5-dialdehyde or 2,5-diformylfuran (DFF).

PRIOR ART

5-HMF is an organic compound derived especially from C6 saccharides such as fructose and glucose. It consists of a furan heterocycle and bears two functional groups, one an aldehyde and the other an alcohol.

Oxidation of 5-HMF leads to the formation of compounds such as:

furan-2,5-dialdehyde or 2,5-diformylfuran (DFF), which results from the sole oxidation of the primary alcohol function of 5-HMF into an aldehyde function, 5-furaldehyde-2-carboxylic acid or 5-formylfuran-2-carboxylic acid (FFCA), which results from the oxidation of the alcohol and aldehyde functions of 5-HMF into an aldehyde function and a carboxylic acid function, 2,5-furandicarboxylic acid (FDCA), which results from the oxidation of the aldehyde and primary alcohol functions of 5-HMF into carboxylic acid functions.

5-HMF has the major drawback of being unstable especially at high temperatures. This generally results in poor purity of the oxidation products, even the selective oxidation products, of 5-HMF.

Despite this drawback, processes for oxidizing 5-HMF have been very widely studied. For example, patent FR 2 669 634 relates to a process for the catalytic oxidation of 5-HMF leading to the synthesis of FDCA. This process consists in oxidizing 5-HMF in alkaline aqueous medium, under a stream of oxygen, in the presence of a lead-activated platinum-based catalyst. The oxidation process leads selectively to FDCA in the form of a salt. Such a process in alkaline medium thus has, primarily, the major drawback of generating large amounts of salts and is therefore difficult to render industrially.

The Applicant thus specifically addressed processes for oxidizing 5-HMF in acidic medium. Moreover, the Applicant Company, seeking to obtain products of high purity without the addition of generally expensive subsequent steps, of complex separation or purification, addressed processes for the selective oxidation of 5-HMF.

Among these processes in acidic medium, the principle of a heterogeneous catalysis appears on first sight to be the most promising pathway. Specifically, reactions under homogeneous catalysis generally require a separation of the dissolved reaction products.

Heterogeneous catalysis is usually characterized by the use of precious metals fixed on various supports. This type of catalysis is particularly sensitive to the impurities contained in the oxidation medium. It is therefore essential, in order for the process to be industrially acceptable, to work with high-purity reagents in order for the catalyst support, or even the catalyst itself, not to be deactivated by poisoning of the active sites.

The Applicant thus finally specifically addressed processes for oxidizing 5-HMF in acidic medium under homogeneous catalysis. However, such processes require relatively low catalyst/reagent ratios in order to be viable at the industrial scale.

Cottier et al. (J. Heterocyclic Chem. (1995), vol. 32, No. 3, pp. 927-930) describes various types of process for preparing DFF. The processes having the best yields are those performed in basic medium, with the presence of co-oxidants other than oxygen and a catalyst such as a (2,2,6,6-tetramethylpiperid-1-yl)oxyl, referred to hereinbelow as Tempo. Catalyses in acidic medium are also described, but, under such conditions, the amount of catalyst required is extremely high (Tempo/5-HMF mole ratio of 2/10), and these catalyses also require the presence of a co-oxidant of metallic type.

Thus, although a very large number of routes exist for preparing one or more 5-HMF oxidation products, they unfortunately all have at least one of the following drawbacks: a low degree of conversion of the 5-HMF, poor selectivity towards DFF after the oxidation process, a poor yield, a high economic cost, a large production of salt(s), the need for a reactor designed for three-phase mixtures, etc. There is thus a real need to develop an improved process for oxidizing 5-HMF which does not have any of the above drawbacks.

SUMMARY OF THE INVENTION

One subject of the present invention is a process for oxidizing 5-HMF, characterized in that it comprises a step of oxidation in the presence of at least an organic acid, a nitroxyl radical, a source of oxygen, and an oxygen-transfer agent.

DETAILED DESCRIPTION

The process for oxidizing 5-HMF according to the invention has in particular the advantage of allowing the preparation of DFF from 5-HMF with a high degree of conversion and also a particularly high yield and selectivity.

Throughout the present application, the terms "selectivity" (S), "conversion" (C) and "yield" (Y) are used with reference to the following definitions:

$C$ (mol %)=((amount of 5-HMF transformed)×100)/ amount of initial 5-HMF $S$ (mol %)=((amount of DFF formed)×100)/amount of 5-HMF transformed $Y$ (mol %)=$S \times C$/100=((amount of DFF formed)×100)/ amount of initial HMF The oxidation process of the present invention may be performed in any type of batch or fixed-bed reactor, under pressure or otherwise. The type of batch reactor may be an autoclave equipped with a variable-speed stirrer and a double-paddle system in the form of an impeller. Preferentially, the reactor is also equipped with a gas inlet tube, connected to a system under pressure equipped with a pressure regulator, and a gas evacuation tube. The reactor may also comprise a cooling system and also a system for measuring and regulating the temperature.

The 5-HMF used in the process that is the subject of the invention may be obtained according to any technique known to those skilled in the art, in particular obtained according to the teaching of documents FR 2 551 754, FR 2 464 260 and WO 2011/124 639. It may also be crude reaction product as described in the documents mentioned previously, said crude reaction product being simply separated from the reaction solvent. Specifically, according to the process of the present invention, it is not necessary, in order to obtain a DFF of high purity after the process, to start with a purified 5-HMF. The term "DFF of high purity" means herein a DFF with a purity of greater than 90%, preferentially greater than 95% and more preferentially greater than 98%.

The organic acid used in the process that is the subject of the invention may be any organic acid with the exception of those bearing a reductive function, especially with the exception of formic acid. Specifically, this organic acid is used as solvent and must therefore be stable under the conditions of the process. The organic acid used in the process that is the subject of the invention may be in particular an aliphatic organic acid that is liquid at room temperature other than formic acid. Preferably, it is chosen from acetic acid and propionic acid.

According to the process that is the subject of the invention, the organic acid is advantageously present in a proportion of from 50% to 99% by weight of the reaction mixture and preferentially 70% to 90% by weight of the reaction mixture.

According to the process that is the subject of the invention, the nitroxyl radical is preferentially chosen from (2,2,6,6-tetramethylpiperid-1-yl)oxyls, referred to hereinbelow as Tempo, which are optionally substituted. More preferentially, the nitroxyl radical is a (2,2,6,6-tetramethylpiperid-1-yl)oxyl substituted in position 4, and even more preferentially is 4-acetoamino(2,2,6,6-tetramethylpiperid-1-yl)oxyl or 4AA Tempo. The Tempo used in the process of the present invention may optionally be immobilized. In the case of an immobilized Tempo, it is advantageously fixed in position 4 to a polymer resin. In the case of an immobilized Tempo, the process may advantageously be performed in a fixed-bed continuous reactor.

According to the process that is the subject of the invention, the nitroxyl radical is advantageously present in catalytic amount. In particular, the nitroxyl radical is present in a proportion of from 0.01% to 15% by weight relative to the weight of 5-HMF, preferentially 1% to 10% by weight relative to the weight of 5-HMF and even more preferentially 2% to 5% by weight relative to the weight of 5-HMF.

According to the process of the present invention, the source of oxygen is preferentially chosen from air and molecular oxygen under pressure and/or in a stream.

The oxygen-transfer agent is, itself, advantageously chosen from nitrogen oxide derivatives. The nitrogen oxide derivatives are preferentially selected from sources of nitrate, nitric oxide (NO) and nitrogen dioxide ($NO_2$). By way of example, the sources of nitrate include nitric acid, ammonium nitrate, alkylammonium nitrates, and alkali metal or alkaline-earth metal nitrates. According to a particular mode of the invention, one or more nitrogen oxide derivatives may be used in the oxidation process. According to a particularly preferred mode of the invention, the nitrogen oxide derivative is nitric acid.

According to the process that is the subject of the invention, the source of nitrate is advantageously present in a source of nitrate/nitroxyl radical ratio of from 0.5/1 to 40/1 in the reaction mixture, preferentially a source of nitrate/nitroxyl radical ratio of from 3/1 to 10/1 in the reaction mixture.

According to the process that is the subject of the invention, there is no particular need to add to the reaction medium a co-catalyst of metallic type especially such as ruthenium chloride, ferric chloride and copper chloride. The Applicant has especially demonstrated that replacement of the oxygen-transfer agent with a co-catalyst of metallic type does not make it possible to convert 5-HMF into DFF. Furthermore, according to the process that is the subject of the invention, the addition of co-catalyst of metallic type in the presence or absence of nitric acid does not afford any notable improvement to the yield of DFF.

According to a most particular embodiment, the ratios between the reagents of the oxidation process according to the invention are established so as to have 2.1% by weight of 4AA Tempo relative to the weight of 5-HMF, a 5-HMF/acetic acid mole ratio of about 0.05 and an $HNO_3$/4AA Tempo mole ratio of 4.

The process according to the invention may be performed in the absence or presence of water. If the process is performed in the presence of water, this water is then present in a proportion of not more than 200% by weight relative to the 5-HMF, and preferentially not more than 50% by weight relative to the 5-HMF.

According to the process of the invention, the reagents are placed in the reactor, this reactor advantageously being purged at least once under pressure. The purging may be performed, for example, at 0.3 MPa of oxygen. The reactor is then heated. The heating may advantageously be performed under pressure of oxygen, preferentially at 0.01 to 5 MPa of oxygen.

During the oxidation process, the reaction medium is kept stirring. The stirring speed is preferentially set at between 800 and 2200 rpm and more preferentially between 1500 and 1700 rpm.

According to an advantageous embodiment, when the temperature inside the reactor reaches about 70° C., the oxygen pressure is adjusted to a reaction atmosphere pressure of between 0.01 MPa and 5 MPa, preferentially between 0.1 MPa and 2 MPa and more preferentially between 0.2 and 0.5 MPa.

The consumption of oxygen during the first step of oxidation of the process according to the invention generally starts at 80° C. Advantageously, the temperature during the first step of oxidation is adjusted to between 50° C. and 150° C., preferentially between 70° C. and 110° C. and more preferentially between 80° C. and 90° C.

According to a preferred embodiment, the first step of oxidation of the process according to the invention lasts from one minute to 5 hours and preferentially from 30 minutes to 2 hours.

At the end of the first step of oxidation of the process according to the invention, the reactor is cooled, for example by simply switching off the heating with removal of the heating mantle, without using the cooling loop.

The stirring in the reactor is reduced, optionally gradually, during the cooling.

Advantageously, when the reactor reaches 40 to 80° C., preferentially 60° C., the stirring is completely stopped and the pressure is reduced to atmospheric pressure.

In a particularly advantageous manner and up to a solids content of 30% by weight of starting 5-HMF, at the end of the first step of oxidation and after cooling, all the components are then in solution, and there are neither any crystals or any precipitates.

The process for oxidizing 5-HMF according to the invention is particularly advantageous since it allows the selective preparation of DFF in a high yield. In particular, the selectivity of oxidation of 5-HMF into DFF during the first step of oxidation is preferentially from 80% to 100% and even more preferentially from 90% to 100%.

After the first step of oxidation of the 5-HMF, the crude reaction product containing the DFF may also contain a certain number of co-products (referred to by this term in the examples). They are generally predominantly products of overoxidation of 5-HMF, in particular FFCA and/or FDCA.

Preferably, and in particular when acetic acid has been chosen as solvent for the first step of oxidation, the process according to the invention also comprises, after the first step of oxidation, a crystallization step. Specifically, acetic acid is a good crystallization solvent for DFF.

The crystallization step may be performed directly in the reactor or in another apparatus, especially during a continuous process. Advantageously, this other apparatus may be a jacketed thermostatic crystallization tank equipped with a stirring system.

During the crystallization step, the stirring speed is advantageously adjusted to a low speed, preferentially to a speed of between 80 rpm and 250 rpm.

Advantageously, the temperature is gradually lowered during the crystallization step, preferentially decreased at a temperature ramp of 10° C./hour.

At the end of the crystallization step, a very low temperature, of the order of about ten degrees, is maintained. Advantageously, the temperature is maintained at from 10 to 15° C. for about one hour with stirring. The medium is then advantageously filtered. By way of example, this may be vacuum filtration on a filter funnel. The crystals thus obtained during this step are then dried in an additional drying step, for example in a vacuum desiccator at room temperature.

The process for oxidizing 5-HMF according to the invention is particularly advantageous since it allows the production of high-purity DFF from a 5-HMF of low purity. The term "5-HMF of low purity" means a 5-HMF derived from a crude reaction product of prior art processes, said crude reaction product being simply separated from the reaction solvent.

According to a particularly advantageous mode of the invention, the dried crystals have a DFF purity of greater than 90% by weight, preferentially greater than 95% by weight and even more preferentially greater than 98% by weight.

The invention will be better understood with the aid of the examples that follow, which are not intended to be limiting and merely present certain embodiments and certain advantageous properties of the DFF in accordance with the invention.

EXAMPLES

Example 1

Preparation of 5-HMF 10 g (79 mmol) of 5-(hydroxymethyl)furfural (referred to herein as 5-HMF, purity of 98%), 0.213 g (1 mmol) of 4-acetoamino(2,2,6,6-tetramethylpiperid-1-yl)oxyl (referred to herein as 4AA Tempo), 100 g (1.67 mol) of acetic acid and 4.35 g of nitric acid at 0.91 mol/l (4 mmol) are placed in a stainless-steel autoclave with an internal volume of 600 ml, sold by the company Parr (model No. 4346), equipped with a variable-speed stirrer and a double-paddle system in the form of an impeller, a gas inlet tube connected to a pressurized bottle equipped with a pressure regulator, a gas evacuation tube, a cooling coil and a system for measuring and regulating the temperature.

The ratios are established so as to have 2.1% by weight of 4AA Tempo, 5 mol % of nitric acid relative to the 5-HMF. The $HNO_3$/4AA Tempo ratio is thus 4.

Once all the reagents have been placed in the autoclave, it is purged once at 0.3 MPa with oxygen and then heated under 0.1 MPa of oxygen. The stirring speed is then adjusted to 1600 rpm. When the reactor reaches 70° C., the oxygen pressure is adjusted to 0.3 MPa. The consumption of oxygen starts at 80° C. The temperature is regulated at 85° C. for 1 hour.

After one hour of contact time, the autoclave is cooled by simply switching off the heating, with removal of the heating mantle, without circulation of water in the cooling loop (which avoids crystallization of the DFF on the coil). The stirring is lowered to 250 rpm during the cooling.

When the reactor reaches 60° C., the stirring is stopped and the pressure is reduced to atmospheric pressure. The autoclave is opened at 60° C., all the components are in solution, and there are neither any crystals nor any precipitates.

A sample of the crude reaction product is taken and analyzed by gas chromatography (GC) and the results are expressed as a percentage of the area distribution.

The composition of the crude reaction product is presented in Table 1.

TABLE 1

| Conversion 5-HMF % | Yield DFF % | Co-products % |
| --- | --- | --- |
| 100 | 94.6 | 5.4 |

For the crystallization step, the reaction medium is transferred into a jacketed thermostatic beaker equipped with an anchor-shaped stirrer. During the crystallization, the stirring speed is set at a speed of 140 rpm.

To start the crystallization, the jacket temperature is set at 50° C. and is then lowered at a temperature ramp of 10° C./hour. At the end of crystallization, the temperature is maintained at 12° C. for one hour with stirring.

After the crystallization step, the medium is filtered under vacuum on a filter funnel.

The crystals thus obtained are dried in a vacuum desiccator at room temperature.

The composition of the crystals after drying is presented in Table 2 (GC analyses and results expressed as a percentage of the area distribution).

TABLE 2

| Yield DFF % | Co-products % |
| --- | --- |
| 97.8 | 2.2 |

The purity of the crystals thus obtained reaches about 98% by simple crystallization of the crude reaction product.

Example 2

Impact of the Source of Oxygen and of the Pressure of the Reaction Atmosphere 10 g (79 mmol) of 5-HMF with a purity of 98%, 0.213 g (1 mmol) of 4AA Tempo, 100 g (1.67 mol) of acetic acid and 4.35 g of nitric acid at 0.91 mol/l (4 mmol) are placed in a reactor identical to that used in Example 1.

The operating conditions are identical to those described in Example 1 without the crystallization step, apart from the fact that the nature of the source of oxygen (oxidizing agent) and the pressure of the reaction atmosphere have changed.

A sample of the crude reaction product is taken and analyzed by GC, and the results are expressed as a percentage of the area distribution.

The composition of the crude reaction product is presented in Table 3.

TABLE 3

Oxidizing agent

| Nature | Pressure in MPa | Conversion 5-HMF % | Yield DFF % | Selectivity DFF % | Co-products % |
|---|---|---|---|---|---|
| $O_2$ | 0.3 | 100 | 94.6 | 94.6 | 5.4 |
| $O_2$ | 5 | 100 | 95.8 | 95.8 | 4.2 |
| Air | 0.6 | 64.9 | 64.9 | 100 | 0.0 |
| Air | 2.5 | 100 | 95 | 95 | 5.0 |

Irrespective of the oxidizing agent engaged, good selectivity of oxidation of 5-HMF to DFF is observed (minimum of 94.6%). However, in order to obtain a maximum conversion (greater than 90%), it is preferable to work with pure oxygen or air at high pressure.

Example 3

Influence of the Oxygen-Transfer Agent 10 g (79 mmol) of 5-HMF with a purity of 98%, 0.213 g (1 mmol) of 4AA Tempo, and 100 g (1.67 mol) of acetic acid are placed in a reactor identical to that used in Example 1. An oxygen-transfer agent is also optionally placed in the reactor in the amounts detailed in Table 4.

The operating conditions are identical to those described in Example 1, without the crystallization step.

A sample of the crude reaction product is taken and analyzed by GC chromatography, and the results are expressed as a percentage of the area distribution.

The composition of the crude reaction product is presented in Table 4.

TABLE 4

Oxygen-transfer agent

| Nature | Agent/Tempo mole ratio | Conversion 5-HMF % | Yield DFF % | Co-products % |
|---|---|---|---|---|
| $HNO_3$ | 5/1 | 100 | 52.7 | 47.3 |
| $HNO_3$ | 9/5 | 100 | 86.6 | 13.4 |
| $HNO_3$ | 4/1 | 100 | 94 | 6 |
| $NaNO_3$ | 4/1 | 100 | 73 | 27 |
| None | 0 | 0 | 0 | 0 |

In the absence of the oxygen-transfer agent, there is no conversion of the 5-HMF to DFF. Furthermore, the nature and content of the transfer agent have an influence on the yield of DFF, with a maximum yield of 94% DFF in the presence of an "agent/4AA Tempo" mole ratio of 4/1.

Example 4

Influence of the Nitroxyl Radical

Various types of nitroxyl radical as detailed in Table 5 and also 10 g (79 mmol) of 5-HMF with a purity of 98%, 100 g (1.67 mol) of acetic acid and 4.35 g of nitric acid at 0.91 mol/l (4 mmol) are placed in a reactor identical to that used in Example 1.

The operating conditions are identical to those described in Example 1, without the crystallization step.

A sample of the crude reaction product is taken and analyzed by GC chromatography, and the results are expressed as a percentage of the area distribution.

The composition of the crude reaction product is presented in Table 5.

TABLE 5

Nitroxyl radical

| Nature | Weight/ 5-HMF % | Conversion 5-HMF % | Yield DFF % | Co-products % |
|---|---|---|---|---|
| 4AA Tempo | 2.1 | 100 | 94.6 | 5.4 |
| Tempo | 2.1 | 75.5 | 74.2 | 1.3 |
| 4-Methoxy Tempo | 2.1 | 96.4 | 93.4 | 3.0 |
| Oxynitrox ® [1] | 0.63 | 100 | 89 | 11 |

[1] Tempo immobilized on polymeric resin sold by the company Arkema

The various nitroxyl radicals are effective for converting 5-HMF to DFF, with a maximum of 94.6% DFF for 4AA Tempo.

Example 5

Influence of the Water Content, of the Solids Content, of the Solvent and of the Content of 4AA Tempo The reagents are placed in a reactor identical to that used in Example 1, with different parameters of the reaction being varied, such as the solids content (SC) presented in Table 6, the solvent presented in Table 7, the presence of water in the reaction medium, presented in Table 8, and the content of 4AA Tempo presented in Table 9.

The other operating conditions are identical to those described in Example 1, without the crystallization step.

A sample of the crude reaction product is taken and analyzed by GC, and the results are expressed as a percentage of the area distribution.

The composition of the crude reaction product is presented in Tables 6, 7, 8 and 9.

TABLE 6

Evaluation of the impact of the solids content (SC)

| SC % | 5-HMF in g | Acetic acid in g | $HNO_3$/Tempo Mole ratio | Conversion 5-HMF % | Yield DFF % | Co-products % |
|---|---|---|---|---|---|---|
| 9 | 10 | 100 | 4/1 | 100 | 94.6 | 5.4 |
| 30 | 35 | 70 | 4/1 | 99.8 | 95.6 | 4.2 |
| 40 | 60 | 60 | 4/1 | 99.4 | 93.2 | 6.2 |

The solids content has little influence on the yields of DFF, with a minimum yield of about 93% at 40% SC.

TABLE 7

Evaluation of the impact of the reaction solvent

| Solvent Nature | 5-HMF in g | $HNO_3$/Tempo Mole ratio | Conversion 5-HMF % | Yield DFF % | Co-products % |
|---|---|---|---|---|---|
| Acetic acid | 100 | 10 | 4/1 | 100 | 94.6 | 5.4 |
| Propionic acid | 100 | 10 | 4/1 | 100 | 85.5 | 14.5 |
| Formic acid | 100 | 10 | 4/1 | 0 | 0 | 0 |

The reaction solvent has an influence on the conversion of 5-HMF to DFF. The yield of DFF decreases by 9.1 points on passing from the acetic medium to the propionic medium. Furthermore, no conversion of the 5-HMF is observed in formic acid medium (reducing). The acetic acid medium is thus preferred for the conversion of 5-HMF to DFF.

TABLE 8

Influence of the water content in the reaction medium

| Water Weight/ 5-HMF % | 5-HMF in g | Acetic acid in g | HNO$_3$/ Tempo Mole ratio | Conversion 5-HMF % | Yield DFF % | Co-products % |
|---|---|---|---|---|---|---|
| 40 | 10 | 100 | 4/1 | 100 | 94 | 6 |
| 20 | 50 | 130 | 4/1 | 98.4 | 91.4 | 7 |
| 0 | 10 | 100 | 4/1 | 100 | 94.6 | 5.4 |

The presence of water in the reaction medium does not create any loss of richness in DFF.

TABLE 9

Influence of the content of nitroxyl radical

| 5-HMF in g | Nitroxyl radical Nature | Weight/ 5-HMF % | HNO$_3$/ Tempo Mole ratio | Conversion 5-HMF % | Yield DFF % | Co-products % |
|---|---|---|---|---|---|---|
| 10 | 4AA Tempo | 0.5 | 4/0.23 | 53.5 | 48.7 | 4.8 |
| 10 | 4AA Tempo | 2.1 | 4/1 | 100 | 94.6 | 5.4 |

The content of 4AA Tempo has an influence on the conversion of 5-HMF to DFF. The increase in the content of catalyst promotes the conversion of the 5-HMF.

Example 6

Impact of a Metallic Co-Catalyst 10 g (79 mmol) of 5-HMF with a purity of 98%, 0.213 g (1 mmol) of 4AA Tempo and 100 g (1.67 mol) of acetic acid are placed in a reactor identical to that used in Example 1. Depending on the tests, nitric acid at 0.91 mol/l in an amount of 4.35 g (4 mmol) and/or 4 mmol of metallic co-catalyst are optionally introduced as indicated in Table 10.

The operating conditions are identical to those described in Example 1, without the crystallization step.

A sample of the crude reaction product is taken and analyzed by GC, and the results are expressed as a percentage of the area distribution.

The composition of the crude reaction product is presented in Table 10.

TABLE 10

| Metallic co-catalyst Nature | mol %/ 5-HMF | Nitric acid mol %/ 5-HMF | Conversion HMF % | Yield DFF % | Co-products % |
|---|---|---|---|---|---|
| None | 0 | 5 | 100 | 94 | 6 |
| FeCl$_3$ | 5 | 0 | 0.7 | 0.7 | 0 |
| CoCl$_2$ | 5 | 0 | 0 | 0 | 0 |
| RuCl$_3$ | 5 | 0 | 1.7 | 1.7 | 0 |
| CuSO$_4$ | 5 | 0 | 1 | 0.7 | 0.3 |
| CuCl | 5 | 0 | 0 | 0 | 0 |
| FeCl$_3$ | 5 | 5 | 100 | 89.1 | 10.9 |
| CoCl$_2$ | 5 | 5 | 100 | 89 | 11 |
| RuCl$_3$ | 5 | 5 | 74.5 | 67.8 | 6.7 |

TABLE 10-continued

| Metallic co-catalyst Nature | mol %/ 5-HMF | Nitric acid mol %/ 5-HMF | Conversion HMF % | Yield DFF % | Co-products % |
|---|---|---|---|---|---|
| CuSO$_4$ | 5 | 5 | 100 | 95.3 | 4.7 |
| CuCl | 5 | 5 | 100 | 92 | 8 |
| Co/Mn/Br | 0.53/0.37/0.44 | 5 | 100 | 70.7 | 29.3 |

Replacement of the oxygen-transfer agent with a co-catalyst of metallic type does not make it possible to convert the 5-HMF into DFF.

Furthermore, the addition of co-catalyst of metallic type in the presence or absence of nitric acid does not afford any appreciable improvement in the yield of DFF.

The invention claimed is:

1. A process for oxidizing 5-hydroxymethyl furaldehyde, comprising at least one step of oxidation in the presence of at least:
   an organic acid,
   a nitroxyl radical,
   a source of oxygen, and
   an oxygen-transfer agent.

2. The process as claimed in claim 1, comprising, after the oxidation step, a crystallization step.

3. The process as claimed in claim 1, wherein the organic acid is chosen from organic acids not bearing a reductive function.

4. The process as claimed in claim 3, wherein the organic acid is chosen from acetic acid and propionic acid.

5. The process as claimed in claim 1, wherein the organic acid is present in a proportion of from 50% to 99% by weight of the reaction mixture.

6. The process as claimed in claim 1, wherein the source of oxygen is chosen from air and molecular oxygen, under pressure and/or in a stream.

7. The process as claimed in claim 1, wherein the nitroxyl radical is chosen from substituted or unsubstituted (2,2,6,6-tetramethylpiperid-1-yl)oxyls.

8. The process as claimed in claim 1, wherein the nitroxyl radical is present in a proportion of from 0.01% to 15% by weight relative to the 5-HMF.

9. The process as claimed in claim 1, wherein the oxygen-transfer agent is chosen from nitrogen oxide derivatives.

10. The process as claimed in claim 1, wherein the oxidation step is performed at a reaction atmosphere pressure of between 0.01 MPa and 5 MPa.

11. The process as claimed in claim 1, wherein the oxidation step is performed at a temperature of between 50° C. and 150° C.

12. The process as claimed in claim 1, wherein the oxidation step is performed in the absence of water or in the presence of an amount of not more than 200% by weight of water, relative to the 5-HMF.

13. The process as claimed in claim 5, wherein the organic acid is present in a proportion of from 70% to 90% by weight of the reaction mixture.

14. The process as claimed in claim 8, wherein the nitroxyl radical is present in a proportion of from 1% to 10% by weight relative to the 5-HMF.

15. The process as claimed in claim 11, wherein the oxidation step is performed at a temperature of between 70° C. and 110° C.

16. The process as claimed in claim 12, wherein the oxidation step is performed in the absence of water or in the presence of an amount of not more than 50% by weight of water, relative to the 5-HMF.

* * * * *